United States Patent
Kulak et al.

(10) Patent No.: US 9,791,355 B2
(45) Date of Patent: Oct. 17, 2017

(54) REACTION VESSEL FOR SAMPLE PREPARATION

(71) Applicant: MAX-PLANCK-GESELLSCHAFT ZUR FÖRDERUNG DER WISSENSCHAFTEN E.V., München (DE)

(72) Inventors: Nils A. Kulak, Gauting (DE); Matthias Mann, Stockdorf (DE); Seyed Babak Azimifar, München (DE); Nagarjuna Nagaraj, München (DE)

(73) Assignee: MAX-PLANCK-GESELLSCHAFT ZUR FÖRDERUNG DER WISSENSCHAFTEN E.V., München (DE)

( * ) Notice: Subject to any disclaimer, the term of this patent is extended or adjusted under 35 U.S.C. 154(b) by 0 days.

(21) Appl. No.: 14/654,283

(22) PCT Filed: Dec. 19, 2013

(86) PCT No.: PCT/EP2013/077297
§ 371 (c)(1),
(2) Date: Jun. 19, 2015

(87) PCT Pub. No.: WO2014/096136
PCT Pub. Date: Jun. 26, 2014

(65) Prior Publication Data
US 2015/0346068 A1  Dec. 3, 2015

(30) Foreign Application Priority Data

Dec. 19, 2012 (EP) .................................... 12198144

(51) Int. Cl.
*C12N 15/10* (2006.01)
*G01N 33/68* (2006.01)
(Continued)

(52) U.S. Cl.
CPC ............. *G01N 1/405* (2013.01); *B01D 15/12* (2013.01); *B01D 15/125* (2013.01); *B01D 15/22* (2013.01);
(Continued)

(58) Field of Classification Search
CPC  B01D 15/12; B01D 15/22; B01D 2200/0631; B01J 19/0093;
(Continued)

(56) References Cited

U.S. PATENT DOCUMENTS 5,137,031 A   8/1992  Guirguis
5,228,988 A   7/1993  Sanford et al.
(Continued)

FOREIGN PATENT DOCUMENTS

DE  102010003223 A1  9/2011
EP  0471570 A1  2/1992
(Continued)

OTHER PUBLICATIONS

International Search Report and Written Opinion for PCT/EP2013/077297 mailed Jul. 4, 2014.
(Continued)

*Primary Examiner* — Jeffrey E Russel
(74) *Attorney, Agent, or Firm* — Roberts Mlotkowski Safran Cole & Calderon, P.C.

(57) ABSTRACT

Disclosed is a sample preparation container for purification and/or enrichment of bio-organic compounds from cellular material, viruses and/or sub-components of these. The container includes a reaction chamber and a chromatography medium. The reaction chamber is for holding the cellular material, etc. and is configured to perform reactions inside. The chromatography medium is configured to purify the bio-organic compounds. The chromatography medium is located at a wall of the reaction chamber, and the wall is
(Continued)

closed or sealed and configured to be opened for obtaining purified bio-organic compounds. The sample preparation container further includes a receiving chamber for receiving the bio-organic compounds, that is adjacent to the chromatography medium such that the chromatography medium separates the reaction chamber from the receiving chamber. The outer face of the receiving chamber is closed and configured to be opened for obtaining purified bio-organic compounds.

3 Claims, 5 Drawing Sheets (51) Int. Cl.
G01N 1/40 (2006.01)
B01D 15/12 (2006.01)
B01D 15/22 (2006.01)
B01L 3/00 (2006.01)

(52) U.S. Cl.
CPC ............ B01L 3/502 (2013.01); C12N 15/101 (2013.01); G01N 33/6842 (2013.01); B01L 2200/0631 (2013.01); B01L 2300/042 (2013.01); B01L 2300/044 (2013.01); B01L 2300/047 (2013.01); B01L 2300/069 (2013.01)

(58) Field of Classification Search
CPC ....... B01L 2200/0631; B01L 2300/042; B01L 2300/044; B01L 2300/047; B01L 2300/069; B01L 2560/00; B01L 2570/00; C12M 1/33; C12M 45/02; C12M 45/06; C12M 45/09; C12M 45/20; C12M 1/40; C12M 21/18; C12M 47/12; C12Q 1/02; C12Q 2523/107; C12Q 2523/301; C12Q 21/06; C12Q 1/37; G01N 1/4005; G01N 1/4022; G01N 1/4044; G01N 1/405; G01N 30/00; G01N 33/50; G01N 33/6842; G01N 33/6848; G01N 33/6851; G01N 2001/4011; G01N 2001/4016; C07K 1/12; C07K 1/122; C07K 1/126; C12P 21/06; C12N 15/1003; C12N 15/101; C07C 7/005; C07C 7/12; C07C 51/47

See application file for complete search history.

(56) References Cited

U.S. PATENT DOCUMENTS

| | | | |
|---|---|---|---|
| 5,746,978 A * | 5/1998 | Bienhaus | C12Q 1/6848 210/143 |
| 6,120,985 A * | 9/2000 | Laugharn, Jr. | B01L 3/5027 435/1.3 |
| 6,153,147 A | 11/2000 | Craig | |
| 6,770,246 B1 | 8/2004 | Husek | |
| 2002/0197631 A1 | 12/2002 | Lawrence et al. | |
| 2006/0141631 A1 * | 6/2006 | Bondarenko | G01N 33/6842 436/86 |
| 2006/0246533 A1 * | 11/2006 | Fathollahi | G01N 33/6842 435/23 |
| 2007/0014690 A1 | 1/2007 | Lawrence et al. | |
| 2010/0081209 A1 | 4/2010 | Brewer | |
| 2012/0202193 A1 | 8/2012 | Heinrich | |
| 2013/0252796 A1 | 9/2013 | Von Stetten et al. | |

FOREIGN PATENT DOCUMENTS

| | | | |
|---|---|---|---|
| EP | 0527562 A2 | 2/1993 | |
| EP | 1033169 A1 | 9/2000 | |
| WO | 02088296 A1 | 11/2002 | |
| WO | 2008103828 A1 | 8/2008 | |
| WO | WO 2009/016431 A1 * | 2/2009 | |
| WO | WO 2011/014372 A1 * | 2/2011 | |
| WO | 2011032530 A1 | 3/2011 | |
| WO | 2011042467 A1 | 4/2011 | |
| WO | 2014096136 A2 | 6/2014 | |

OTHER PUBLICATIONS

Picotti, et al., "Full Dynamic Range Proteome Analysis of S. cerevisiae by Targeted Proteomics", Cell 138, 795-806, Aug. 21, 2009, pp. 795-806.

Marguerat, et al., "Quantitative Analysis of Fission Yeast Transcriptomes and Proteomes in Proliferating and Quiescent Cells", Cell 151, 671-683, Oct. 26, 2012, pp. 671-683.

Rappsilber, et al., "Stop and Go Extraction Tips for Matrix-Assisted Laser Desorption/Ionization, Nanoelectrospray, and LC/MS Sample Pretreatment in Proteomics", Analytical Chemistry, vol. 75, No. 3, Feb. 1, 2003, pp. 663-670.

Nagaraj, et al., "System-wide Perturbation Analysis with Nearly Complete Coverage of the Yeast Proteome by Single-shot Ultra HPLC Runs on a Bench Top Orbitrap", Molecular & Cellular Proteomics 11.3, 2012, 11 pages.

Gunaratne, et al., "Extensive Mass Spectrometry-based Analysis of the Fission Yeast Proteome", Molecular & Cellular Proteomics 12.6, 2013, pp. 1741-1751.

Leon, et al., "Quantitative Assessment of In-solution Digestion Efficiency Identifies Optimal Protocols for Unbiased Protein Analysis", Molecular & Cellular Proteomics 12: 10.1, pp. 2992-3005, 2013.

Wisniewski, et al., "Extensive quantitative remodeling of the proteome between normal colon tissue and adenocarcinoma", Molecular Systems Biology 2012, 15 pages.

Ghaemmaghami, et al., "Global analysis of protein expression in yeast", Nature, vol. 425, Oct. 16, 2003, pp. 737-741.

Picardi, et al., "Protease bias in absolute protein quantitation", vol. 9 No. 6, Jun. 2012, Nature Methods, pp. 524-525.

Nieduszynski, et al., "OriDB: a DNA replication origin database", Nucleic Acids Research, 2007, vol. 35, 7 pages.

* cited by examiner

REACTION VESSEL FOR SAMPLE PREPARATION

CROSS-REFERENCE TO RELATED APPLICATIONS

The present Application is a U.S. National Phase of PCT/EP2013/077297 filed on Dec. 19, 2013 which claims priority to European patent application No. 12198144.3 filed on Dec. 19, 2012. The disclosure of the PCT Application is hereby incorporated by reference into the present Application.

This invention relates to a sample preparation container for purification and/or enrichment of bio-organic compounds from cellular material, viruses and/or sub-components of said cellular material and/or viruses, the container comprising a reaction chamber and a chromatography medium; wherein said reaction chamber is for holding said cellular material, viruses and/or sub-components of said cellular material and/or viruses and is configured such that at least one of the following reactions can be performed therein: lysis, e.g. by sonication and/or boiling; chromatographic purification; reduction; alkylation; and enzymatic reactions such as proteolysis; wherein said chromatography medium is configured to purify and/or enrich said bio-organic compounds; wherein (a) said chromatography medium is located at a wall of said reaction chamber, and said wall is closed or sealed and configured to be opened for obtaining purified and/or enriched bio-organic compounds; or (b) said sample preparation container further comprises a receiving chamber for receiving said bio-organic compounds, said receiving chamber being adjacent to said chromatography medium such that said chromatography medium separates said reaction chamber from said receiving chamber, and the outer face of said receiving chamber is closed and configured to be opened for obtaining purified and/or enriched bio-organic compounds.

In this specification, a number of documents including patent applications and manufacturer's manuals are cited. The disclosures of these documents, while not considered relevant for the patentability of the present invention, is herewith incorporated by reference in its entirety. More specifically, all the referenced documents are incorporated by reference to the same extent as if each individual document was specifically and individually indicated to be incorporated by reference.

Sample preparation methods used to enrich certain biological materials including cell lysis are currently applied in essentially all fields of biological research. The extraction, purification, and processing of DNA, RNA, and proteins are the initial steps for the in-vitro analysis of these and other biological materials. Current methods involve pre-clarification steps and the transfer of these materials to different reaction vessels to avoid clogging of analysis devices such as analytical columns and sometimes to enrich the desired biological materials. The purity of the sample is viewed to be important in certain fields of biological research such as crystallography and electron-microscopy. These pre-clearing and sample transfer steps display some major disadvantages in terms of sample loss, extended sample preparation times, unwanted modifications for instance of proteins to be analyzed, introduction of contaminations, potential hazards in handling harmful or infectious materials, and material costs. Yet, they are generally viewed as being indispensable.

Sample loss occurs at the step of pre-clearing of crude lysates because of incomplete extraction and extended contact to vessel surfaces where sample absorption occurs. Current solutions to reduce sample loss include very stringent extraction methods and low binding surfaces on the reaction tubes.

Repeated sample transfers take time; especially hands-on where the researcher has to be present and needs to handle the sample. Extended UV-light or oxygen exposure may damage the sample and can lead to unwanted chemical modifications. Solutions to these issues are the use of light protected vessels and of shield-gas, respectively. However, these measures makes sample handling yet more difficult and time-consuming. Furthermore, contaminations may be introduced during sample transfers between vessels and can presently only be avoided by working at expensive clean benches, under laminar-flow, or with similar precautions. Moreover, harmful samples such as pathogens introduce the risk to contaminate the person or machines getting in contact with the sample tubes. Finally, any of these inefficiencies in sample preparation as well as the use of more than a minimum amount of single-use materials can increase processing costs significantly.

Devices such as pipette tips comprising chromatographic material are known in the art and available from several manufacturers and include Pierce C-18 tips (Thermo Fisher) and C18-SD cartridges (3M). These devices are open at both ends. Such devices are not suitable for sample preparation in a single reaction vessel. Sample preparation in this context includes the preparation of peptides and polypeptides for mass spectrometric analysis from cellular material and/or the preparation of nucleic acids for expression profiling from cellular material.

Rappsilber et al. (Anal Chem.; 75(3):663-70 (2003)) describe a device also referred to as "StageTips" which is open at both ends and allows the performance of chromatography in a compact format.

European Patent Application EP 1 033 169 describes a sorbent cartridge for solid phase extraction. The cartridge according to EP 1 033 169 is characterized as having an opening at the distal end of the tip, this opening being designated with reference (18), which opening is essential for the functioning of the cartridge. The distal end is where the solid phase extraction material, preferably in the form of beads, is provided. While a cap (32) closes the proximal end of the sorbent cartridge, the distal end needs to be open or to be opened for contacting raw material with the beads. The bottom part of the device of the present invention, which is the "distal end" when using the nomenclature of EP 1 033 169, is made of a wall which is closed or sealed, or, provided in the form of a closed receiving chamber. Loading with raw material is nevertheless possible, namely at the upper ("proximal") end. Sample loading in accordance with EP 1 033 169, however, is only possible when the distal end is open.

In view of the limitations of the means and methods available in the art, the technical problem underlying the present invention can be seen in the provision of devices and methods for sample preparation, wherein said sample preparation is to be effected in a single reaction vessel without any transfer steps.

Accordingly, this invention relates in a first aspect to sample preparation container for purification and/or enrichment of bio-organic compounds from cellular material, viruses and/or sub-components of said cellular material and/or viruses, the container comprising a reaction chamber and a chromatography medium; wherein said reaction chamber is for holding said cellular material, viruses and/or sub-components of said cellular material and/or viruses and is configured such that at least one of the following reactions can be performed therein: lysis, e.g. by sonication and/or boiling; chromatographic purification; reduction; alkylation; and enzymatic reactions such as proteolysis; wherein said chromatography medium is configured to purify and/or enrich said bio-organic compounds; wherein (a) said chromatography medium is located at a wall of said reaction chamber, and said wall is closed or sealed and configured to be opened for obtaining purified and/or enriched bio-organic compounds; or (b) said sample preparation container further comprises a receiving chamber for receiving said bio-organic compounds, said receiving chamber being adjacent to said chromatography medium such that said chromatography medium separates said reaction chamber from said receiving chamber, and the outer face of said receiving chamber is closed and configured to be opened for obtaining purified and/or enriched bio-organic compounds.

The term "sample" refers to a composition which is ready for subsequent analysis. For example, if said bio-organic compounds are peptides or polypeptides, a preferred subsequent analysis is by mass spectrometry. The sample preparation container according to the present invention is a means for obtaining such sample. Generally speaking, said sample comprises or consists of said purified and/or enriched bio-organic compounds, herein also referred to as "analytes".

In general, the sample preparation container may be cone-shaped, box-shaped or cylindrical. The volume of the container may be suited for sample volumes from 10 µl to 150 µl, including 20, 30, 40, 50, 60, 70, 80, 90 and 100 µl as well as any larger volume also above 150 µl. However the total volume of the sample preparation container may be significantly higher than the volume it is suited for. For example in case of a cone-shaped container, the base radius may be between 1 and 5 such as 1.5, 2 or 3 mm and the height may be between 10 and 150 such as 25 mm.

It is understood that a reaction chamber which is configured such that lysis can be performed therein is configured for performing the art-established lysis methods which include, but are not confined to, sonication, bead-milling and/or boiling.

In case of option (a), the preparation container may further comprise near the wall which is closed or sealed a coupling, e.g. a screw coupling, for coupling within an external receiving chamber. Such external receiving chamber comprises the corresponding counterpart of the coupling, e.g. a male screw thread matching a female screw thread of preparation container. The external receiving chamber may additionally comprise opening means which are configured to open the wall when tightly attached to the wall. These means may be a sharp-edged extension at the end of a screw thread which penetrates the wall when the receiving chamber is tightly screwed in the screw coupling of the preparation container. Consequently, the wall may be of a thin-walled rigid plastic material or flexible plastic material, both configured to be penetrated with said sharp-edged extension.

In case of option (b), the outer face of the receiving chamber, i.e., the free end of the receiving chamber which is opposite to the chromatography medium and the reaction chamber, may be thin-walled such that it can be cut off by scissors or a scalpel. For example, when the container is cone-shaped, the outer face may be the tip of the cone which can be detached for obtaining purified and/or enriched bio-organic compounds.

The container according to the invention provides for sample preparation in a single reaction vessel. The present inventors found out that pre-clearing and sample transfer steps are not only disadvantageous but also dispensable for purifications such as polypeptide or peptide enrichment or purification of the protein proteolysis for subsequent analysis by mass spectrometry based proteomics. This finding is particularly advantageous for membrane and nucleic acid binding proteins, mainly because complete solubilization of such proteins in liquids is difficult and may even be impossible under certain circumstances due to their biochemical behavior. In particular, the inventors found that sample lysis, sample modification, enzymatic reaction, purification and enrichment can all be performed in a single reaction vessel. This single vessel solution reduces sample loss significantly, which is most prominent when working with miniscule sample quantities. The invention allows the analysis of very small sample quantities or very low number of cells. Furthermore, performing all reactions in a single container reduces processing time, especially hands-on time. These improvements enable automation of the processing step with a simple combination of state of the art machineries to a much higher degree than previously possible.

Unwanted modifications of analytes such as proteins and nucleic acids caused by sample preparation are reduced because of enhanced sample preparation speed. The high efficiency of the procedure reduces the quantity of chemicals needed as well as the amount of single-use tubes or tips leading to cost reduction; accordingly the automation of the processing steps reduces hands-on time, costs in terms of work time, and costs in terms of single-use devices.

It is understood that the term "comprising" includes "consisting of". Also, it is understood that "comprising" when followed by a list of reagents, provides for a closed list of reagents, but does not exclude the presence of further compounds which compounds are not viewed as reagents. A compound which would not be viewed as a reagent is for example water. This applies also to buffered solutions.

In a preferred embodiment, said bio-organic compounds or analytes comprise at least one of the following: proteins; peptides; polypeptides; nucleic acids, e.g. deoxyribonucleic acids and ribonucleic acids; lipids including fatty acids; and metabolites.

Generally speaking, a bio-organic compound is an organic compound that naturally occurs in biological systems. An organic compound is a compound comprising one or more carbon atoms. A biological system may be an organism including unicellular and multicellular organisms, a tissue, a cell type from an organism or a tissue, cells in culture, a sub-component of cellular material such as an organelle, organelles including mitochondria, chloroplasts, lysosomes, peroxisomes, Golgi apparatus, endoplasmatic reticulum, nucleolus, nucleus, ribosomes, microtubuli, centrioles and proteasomes. Biological systems furthermore include viruses and sub-components thereof. The term "sub-components" includes macromolecular assemblies.

Peptides and polypeptides are polycondensates of amino acids, preferably of the twenty naturally occurring amino acids. Typically peptides contain between two and thirty amino acids, whereas polypeptides contain more than thirty amino acids.

Nucleic acids are polycondensates of nucleotides. The term "nucleic acid" in accordance with the invention includes DNA, such as cDNA and genomic DNA, and RNA. RNA comprises all forms of RNA including mRNA, non-coding RNA, tRNA and rRNA. Examples of non-coding RNAs include siRNAs, miRNAs, repeat-associated RNAs, small nucleolar RNAs and small nuclear RNAs.

The term "lipid" is well known in the art and relates to predominantly lipophilic/hydrophobic molecules which may carry a polar headgroup, thereby rendering the lipid molecule amphiphilic. Lipids include simple lipids such as hydrocarbons (triacontane, squalene, carotinoids), alcohols (wax alcohol, retinol, cholesterol, linear mono- or polyhydroxylated hydrocarbons, preferably with two to about 30 carbon atoms), ethers, fatty acids and esters such as mono-, di- and triacylgylcerols. Furthermore included are complex lipids such as lipoproteins, phospholipids and glycolipids. Phospholipids in turn comprise glycerophospholipids such as phosphatidic acid, lysophosphatidic acid, phosphatidylgylcerol, cardiolipin, lysobisphosphatidic acid, phosphatidylcholine, lysophosphatidylcholine, phosphatidylethanolamine, phosphatidylserine, phosphatidylinositol and phosphonolipids. Glycolipids include glycoglycerolipids such as mono- and digalactosyldiacylgylcerols and sulfoquinovosyldiacylgylcerol. Also included by the term "lipid" according to the present invention are sphingomyelin, glycosphingolipds and ceramides.

The term "metabolites" is commonly defined as small molecules involved as intermediates and products in metabolism and signaling. These include metabolites categorized as metabolic intermediates, signaling molecules such as hormones, and secondary metabolites.

In a further preferred embodiment, the container comprises a lid, said lid being configured to seal an opening of the reaction chamber and configured to allow feeding of a sample, e.g. by penetration with a needle, and preferably configured to self-reseal after feeding. This preferred embodiment provides a (entirely) closed sample preparation container.

The option that a lid is configured to seal the tube readily enables working under shield gas where necessary which reduces oxidations. Sealing the tube also significantly reduces contaminations introduced during sample preparation. A clean sealed device, e.g. with a penetrable rubber lid guarantees significant reduction of contaminations. At the same time, a sealed vessel also prevents the sample to contaminate the outside, making the work with harmful or toxic materials safer and more feasible.

It is preferred that the lid may be fused with the rest of the chamber, e.g. by ultrasonic welding. Alternatively, this lid may be glued to the rest of the chamber. The lid may be of any material which can be penetrated by a sharp object, e.g. a needle or a lancet. In addition, the lid may be also configured to reseal after penetration with the sharp object.

As an alternative to said lid, said reaction chamber may be open. Preferably, the opening is at the top. In that case it is preferred that the chromatography medium is located at the bottom of said reaction chamber. The terms "top" and "bottom" are defined with respect to the direction of gravity. Gravity is a preferred driving force for performing chromatography.

In a further preferred embodiment, the surface of said chromatography medium is configured to act as a filtration surface and/or comprises a further filtration layer and/or reactive layer, said surface or layer facing the interior of said reaction chamber.

The option that the surface of said chromatography medium is configured to act as a filtration surface and/or comprises a further filtration layer and/or reactive layer allows to remove microscopic and/or mesoscopic impurities from the sample and, to the extent said layer is reactive, allows to perform further chemical reactions. The filtration may be performed by a mesh which is incorporated in the filtration surface. In addition, the mesh may be coated with reactive material, e.g. chemically reactive groups or enzymes such as Peptide-N-Glycosidases (PNGases) which is acting as reactive layer. Alternatively, the filtration may be performed by a woven filter or paper filter. In this case, the woven material or the paper may be coated or treated with a reactive material as well.

Alternatively, said filtration surface, filtration layer and/or reactive layer may be dispensable, in particular if said chromatography medium is constructed to achieve lower backpressures such as by using larger chromatography particle sizes such as 5 μm, 10 μm and more or by using polymeric materials such as micro- or macro-porous poly (styrene-divinyl benzene) and thereby provide a reduced risk of clogging.

In a further preferred embodiment of aspect (b) of the main embodiment as well as of the above disclosed preferred embodiments, to the extent they refer back to embodiment (b) of the main embodiment, the container further comprises a seal wherein said seal is configured to seal said receiving chamber and configured for obtaining said purified and/or enriched bio-organic compounds. For example, the seal may be at the outer face of the receiving chamber or may fully replace said outer face.

As for the aforementioned lid, it is also preferred that this seal may be fused with the receiving chamber, e.g. by ultrasonic welding. Alternatively, said seal may be glued to the receiving chamber like the lid may be glued to the reaction chamber. Consequently, the seal may also be of any material which can be penetrated by a sharp object, e.g. a needle or a lancet and may be configured to reseal after penetration with the sharp object.

In a further preferred embodiment, said container comprises at least one of: polypropylene; polyethylene; material configured to conduct heat, microwaves, shockwaves, sound waves and/or electricity; material with low binding surface; material which is transparent, opaque or selectively transmitting electromagnetic radiation, preferably light, more preferably UV-radiation.

The option that the container comprises material being configured to conduct heat, microwaves, shockwaves, sound waves or electricity, may enhance the different forms of lysis, e.g. by sonication or boiling. A material which is configured to conduct heat may be a metal, e.g. copper and/or silver and/or gold and/or aluminum or hard plastics. Metal may be coated at the outer or inner part of the container. Additionally, said metal is also configured to conduct shockwaves or sound waves in case of sonication. In case of microwaves being applied to the container, it is preferred that the container mostly comprises plastic material.

In a further preferred embodiment, at least one inner wall of the sample preparation container has at least partially low binding and/or low retention characteristics, preferably by an at least partial coating with polytetrafluoroethylene.

Alternatively, the low retention characteristics may result from a very high fluid-repellence, e.g. superhydrophobicity. The high fluid-repellence may be achieved by nanocoatings having a high contact angle, i.e. the angle between the fluid and the solid surface of the inner wall, preferably of more than 150°. The low retention characteristics may also be achieved by surface treatment, e.g. by forming a micronsized papilla-like structure.

In a second aspect, the present invention provides a receiving chamber configured to be coupled to the sample preparation container according to the invention in accordance with item (a) of the main embodiment, and configured to receive purified and/or enriched bio-organic compounds.

In a preferred embodiment of the second aspect, said receiving chamber comprises a coupling element, preferably a screw thread, which is configured to be coupled to a corresponding coupling element, preferably a corresponding screw thread, of a sample preparation container according to the invention in accordance with item (a) of the main embodiment.

This aspect of the invention provides for a separate receiving chamber to the extent the sample preparation container according to the invention does not already comprise such receiving chamber. The mentioned configuration to receive purified and/or enriched bioorganic compounds may be implemented such that said receiving chamber, when coupled to said sample preparation container is separated from the reaction chamber in said container by said chromatography medium. Furthermore and analogous to item (b) of the main embodiment, the receiving chamber in accordance with the second aspect is closed with the exception of those features which provide for a configuration to receive purified and/or enriched bioorganic compounds which configuration may be implemented by the mentioned coupling element. The closed outer face is preferably configured to be opened for obtaining purified and/or enriched bioorganic compounds from said receiving chamber.

Figure 1:
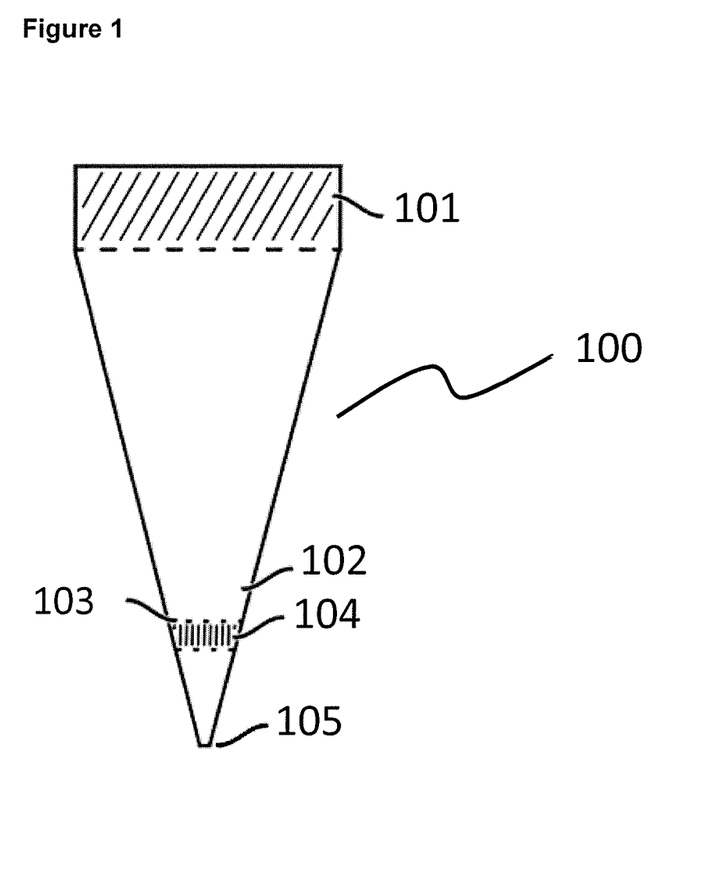
FIG. 1: Exemplary embodiment of a sample preparation container according to the invention. Below is a description of the elements indicated by the reference numerals.

FIG. 1 shows an exemplary embodiment of the sample preparation container 100 according to the invention. The sample preparation container 100 comprises a self-sealing rubber lid or rubber plug 101, a reaction chamber 102, a surface of a chromatography medium 104 acting as a filtration surface 103. A seal 105 is used to completely seal the reaction chamber 102 before the sample lysis.

The self-sealing rubber lid or rubber plug 101 can be penetrated by a needle or several needles to introduce samples, chemicals or shield gas. In addition the rubber lid or rubber plug 101 reseals after removal of the needle. The reaction chamber 102 is constructed for certain reactions such as cell lysis by sonication, protein alkylation, e.g. by iodoacetamide, and proteolysis. The reaction chamber 102 is preferably of polypropylene or polyethylene. The inner walls of the sample preparation container 100 preferably have low retention characteristics. Therefore it may be coated with polytetrafluourethylene (PTFE).

Next to the reaction chamber 102 is a chromatography medium 104 which is used to bind, purify and/or in which the cellular material of interest. In this context the matrix can be designed to perform multi-dimensional chromatography which may be effected by using multiple stacks of chromatography media. The surface 103 after chromatography medium acts as a filtration surface. However, also other surfaces could be applied on top of the surface 103 of the chromatography medium, for example a non-binding filtration matrix such as Millipore filter.

At the end of the sample preparation container 100 opposing the self-sealing rubber lid 101, a seal 105 is formed which is used to completely seal the reaction chamber before sample lysis. Since the sample preparation container is of polyethylene, the seal can be opened by a pair of scissors or a knife such that washing, purification and elution steps can be performed subsequently. Therefore, it is preferred that at this part of the sample preparation container 100 the thickness of the wall is decreased compared to the rest of the sample preparation container 100.

In this embodiment, the sample preparation container 100 is cone shaped. Consequently, the seal 105 can easily be removed by scissors compared to a solely cylindrical sample preparation container 100.

Figure 2:
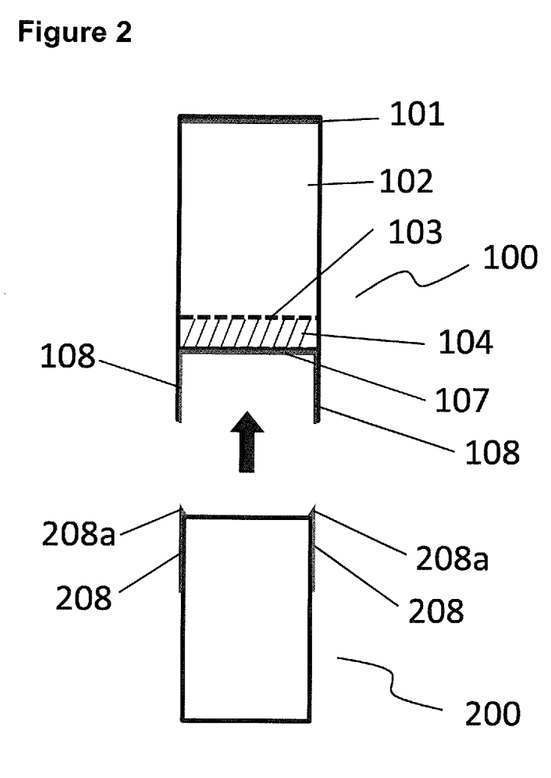
FIG. 2: Exemplary embodiment of a system comprising a sample preparation container and a receiving chamber according to the invention. Below is a description of the elements indicated by the reference numerals.

FIG. 2 shows an exemplary embodiment of a system comprising a sample preparation container 100 and a receiving chamber 200 according to the invention. In this embodiment, the sample preparation container 100 may have a cylindrical shape. Instead of a seal 105 on the opposite side of the self-sealing rubber lid rubber plug 101, the sample preparation container 100 comprises a wall 107 which is closed and sealed, wherein that wall 107 being configured to be opened for obtaining purified and/or enriched by bioorganic compounds. Thus, the wall 107 has a small thickness in comparison to the other walls of the sample preparation container 100. Consequently, the wall 107 can easily be penetrated with any sharp-edged object.

FIG. 2 further shows a receiving chamber 200 which is configured to receive said purified and/or enriched by bio-organic compounds from the sample preparation container 100. The upper side of the receiving chamber 200 may therefore be open. Alternatively, the upper side of the receiving chamber is sealed and the seal is opened immediately before the receiving chamber 200 is receiving said purified and/or enriched by bio-organic compounds from the sample preparation container 100.

The sample preparation container 100 further comprises a screw thread 108 in the vicinity of the wall 107 which is configured to be coupled with a corresponding screw thread 208 of the external receiving chamber 200. In order to be coupled with the sample preparation container 100 the receiving chamber 200 comprises a screw thread 208 which fits to the corresponding screw thread 108 of the sample preparation container 100. In addition, the screw thread 208 of the receiving chamber 200 has a sharp-edged extension 208a at the end of the screw thread 208 which is facing the sample preparation container 100. When the receiving chamber 200 is coupled to the sample preparation container 100 by the screw coupling of both screw threads 108 and 208, the sharp-edged extension 208a penetrates the wall 107 of the sample preparation container and the purified and/or enriched by bio-organic compounds can be received through the penetrated wall 107.

After receiving the bio-organic compounds, the receiving chamber 200 can be decoupled for further use.

In a third aspect, the present invention provides a method of preparing purified and/or enriched bio-organic compounds from cellular material, viruses and/or sub-components of said cellular material and/or viruses, said method comprising (a) introducing said cellular material, viruses and/or sub-compounds of said cellular material and/or viruses into a reaction chamber of a container, said container further comprising a chromatographic medium and a receiving chamber, said chromatographic medium separating said reaction chamber from said receiving chamber, wherein the outer face of said receiving chamber is closed and configured to be opened for obtaining said purified and/or enriched bio-organic compounds; (b) disrupting said cellular material, viruses and/or sub-components of said cellular material and/or viruses inside said reaction chamber; and (c) allowing the result of step (b) to pass through said chromatographic medium, thereby obtaining said purified and/or enriched bio-organic compounds in said receiving chamber; wherein the bio-organic compounds comprise at least one of the following: proteins; peptides; polypeptides; nucleic acids such as deoxyribonucleic acids and ribonucleic acids; lipids including fatty acids and metabolites; and wherein said method is exclusively performed in said container.

Said introducing can be effected by any means, including an injection needle which preferably is used in this case where the reaction chamber of said container is closed with a lid, preferably a self-sealing rubber lid. Other means of introducing, in particular in those cases where said reaction chamber is open instead of being closed by a lid include pipetting.

The term "disrupting" has the meaning as established in the art. It refers to the disintegration of said cellular material, viruses and/or sub-components thereof, thereby rendering the interior constituents of said cellular material, viruses and sub-components thereof accessible for analysis. Preferred means of disrupting are detailed further below.

Said allowing in accordance with step (c) may comprise or consist of placing the container such that the reaction chamber is located above the chromatographic medium such that gravity, centrifugation and/or increased pressure provides for the result of step (b) to pass through said chromatographic medium; and/or opening the receiving chamber which opening may not only provide for passing the result of step (b) through the chromatographic medium, but furthermore obtaining said purified and/or enriched bio-organic compounds. The term "obtaining" refers to a removal of said purified and/or enriched bio-organic compounds from the receiving chamber, for example for the purpose of analysis.

Figure 3:
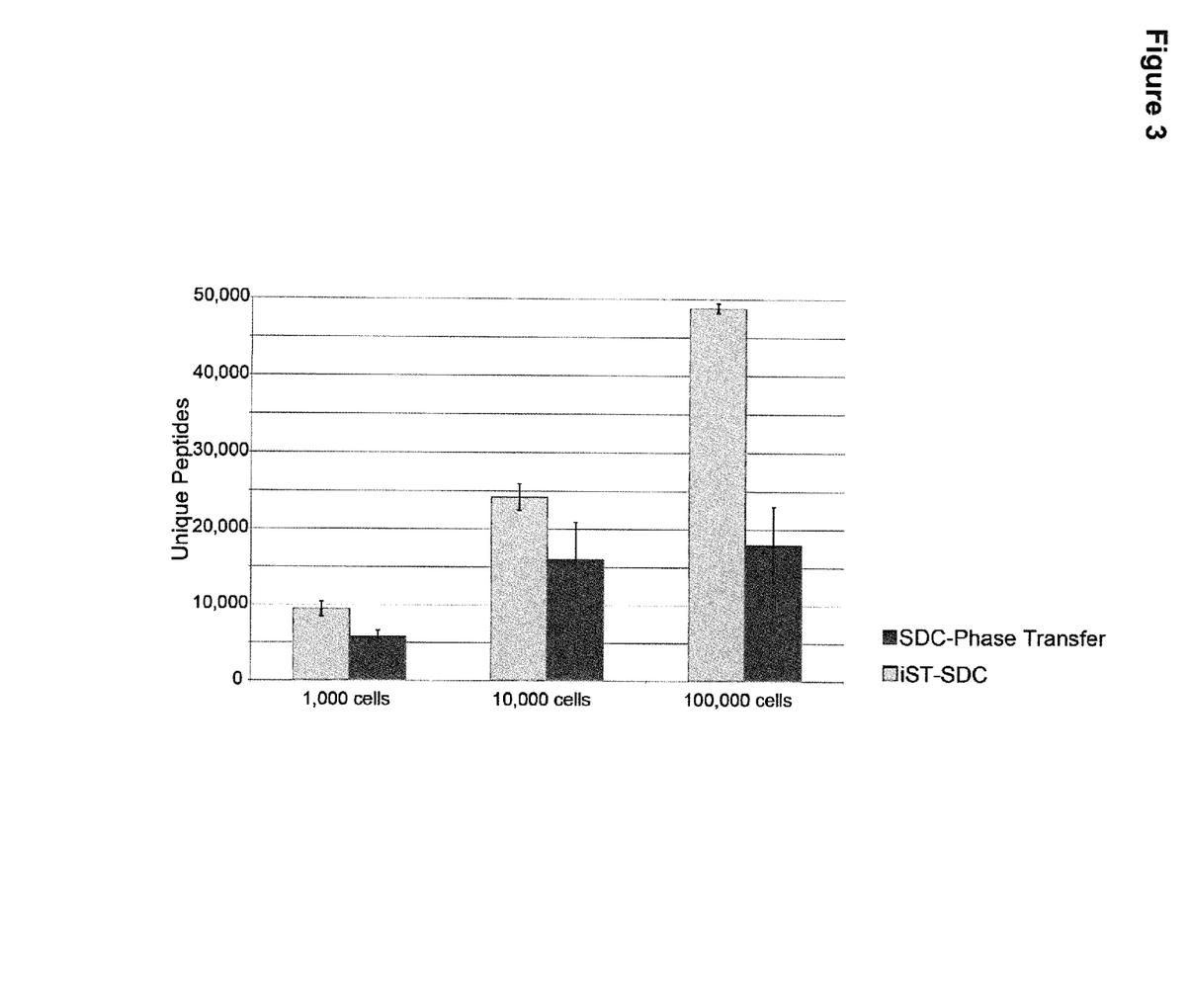
FIG. 3: Comparison of the method of the present invention to a published SDC based in-solution protocol. The latter method is the preferred method according to the state of the art; see Leon et al. (Molecular & cellular proteomics 12 (10), 2992 (2013)). Shown are median unique peptide identifications of technical triplicates±s.e.m.

A key aspect of the present invention is that the method is exclusively performed in said container once said cellular material viruses and/or sub-compounds thereof have been introduced in accordance with step (a). This avoids cumbersome transfer steps which may entail sample loss or contamination as detailed in the background section herein above. FIG. 3 provides evidence of superior performance as compared to art-established procedures. A practical application is shown in Example 2. The method is capable to identify and quantify entire proteomes such as those described in this Example (*Saccharomyces cerevisiae* and *Schizosaccharomyces pombe*). The improved accuracy as afforded by the present invention inter alia allows to estimate protein copy numbers of the entire proteome. Copy number values are especially valuable for systems biology, systems modeling (they provide initial and/or steady state amounts of proteins) as well as monitoring of biological activities such as protein degradation.

In a preferred embodiment, said disrupting is effected by (a) sonication; (b) boiling in the presence of a chaotropic agent and/or a denaturing agent; and/or (c) bead milling in the presence of a physical agent such as milling beads. These are common means of disrupting and can be employed by the skilled person without further ado.

In a preferred embodiment of both the first and the third aspect of the present invention, said chromatography medium comprises (a) at least one of the following materials: reversed-phase materials, cation-exchange materials, anion-exchange materials, mixed-mode ion-exchange materials, ion-complexing materials, an affinity-coupled matrix being antibody-coupled and/or lectin-coupled; and/or (b) two or more stacks of different chromatography media.

Preferred chromatographic materials are the reversed phase materials poly(styrene-divenyl benzene), C4, C8, C18 material as used in Example 1, cation exchange material such as sulfonated binding surfaces, and anion exchange material such as a quaternary ammonium ions as binding surface.

Two or more stacks or layers of different chromatography media may be used to implement two or more chromatography steps when using said container according to the first aspect and/or performing step (c) of the method according to the third aspect.

In a further preferred embodiment of the container according to the first aspect or the method according to the third aspect, (a) said bio-organic compounds comprise proteins, peptides and/or polypeptides and said container is characterized by one, two, three or all of the following (i) to (iv): (i) said container comprises a protease, (ii) said container comprises an alkylating agent; (iii) said container comprises a standard for mass-spectrometric analysis; and (iv) the pH-value in said container is between 8 and 9, preferably 8.5; and/or (b) said bio-organic compounds comprise nucleic acids and said container is characterized by one, two or all of the following: (i) said container comprises one or more nucleases, preferably including an endonuclease; (ii) said container comprises reagents for nucleic acid amplification, preferably by PCR, and (iii) the pH-value in said container is between 8 and 9, preferably 8.5.

In another preferred embodiment of the container according to the first aspect or the method according to the third aspect, (a) said bio-organic compounds comprise one or more proteins, peptides and/or polypeptides and said container is characterized by one, two, three, four, five, six, seven or all of the following (i) to (viii): (i) said container comprises a detergent, preferably SDC; (ii) said container comprises a reducing agent, preferably TCEP; (iii) said container comprises an alkylating agent, preferably chloroacetamide; (iv) the pH-value in said container is between 7 and 9, preferably 8 and 9, more preferably 8.5; (v) said container comprises a standard for mass-spectrometric analysis; (vi) said container comprises a chaotropic agent, preferably GdmCl; (vii) said container comprises an analyte stabilizing chemical such as an antioxidant and/or a UV-absorbant; and (viii) said container comprises at least one enzyme selected from proteases, preferably trypsin and/or Lys-C; glycosidases, preferably PNGase F; and kinases; and/or (b) said bio-organic compounds comprise nucleic acids and said container is characterized by one, two or all of the following: (i) said container comprises one or more nucleases, preferably including an endonuclease; (ii) said container comprises reagents for nucleic acid amplification, preferably by PCR; and (iii) the pH-value in said container is between 8 and 9, preferably 8.5; and/or (b) said bio-organic compounds comprise nucleic acids and said container is characterized by one, two or all of the following: (i) said container comprises one or more nucleases, preferably including an endonuclease; (ii) said container comprises reagents for nucleic acid amplification, preferably by PCR; and (iii) the pH-value in said container is between 7 and 9, preferably between 8 and 9, more preferably 8.5.

The above sub-items (i) through (viii) of item (a) are presented in the order of preference.

Depending on the type of application and/or the type of bio-organic compounds to be purified and/or enriched, said container may be pre-filled with one or more agents, which agents are useful, required and/or specific for purification and/or enrichment of the specific class of bio-organic compounds under consideration. Item (a) provides agents and/or conditions suitable for purification and/or enrichment of proteins, peptides and/or polypeptides.

A preferred detergent is sodium deoxycholate (SDC).

A preferred reducing agent is TCEP.

Preferred alkylating agents are iodoacetamide and chloroacetamide. Particularly preferred is chloroacetamide (CAA).

Particularly preferred is the combined use of an alkylating agent which is chloroacetamide and a reducing agent which is TCEP.

The pH-value in accordance with item (a) or (b), respectively, may be established by pre-filling the container with buffer material, either in the form of a buffered aqueous solution or in the form of the dry constituents required for the preparation of a buffered solution.

A preferred standard for mass spectrometric analysis is a SUPER-SILAC standard as described in WO2011/042467. Typically, said standard exhibits an isotope distribution which deviates from the naturally occurring isotope distribution. For example, it may be enriched with regard to heavy or light isotopes. Preferably, and as disclosed in WO2011/042467, such standard is obtained by a method for preparing a standard mixture for quantifying one or a plurality of first biomolecules in a sample, comprising extracting a plurality of second biomolecules comprising one or a plurality of reference biomolecules from a mixture of at least two different cell populations, wherein said at least two different cell populations are populations of (i) cells of different cell types, (ii) cells from different cell lines; (iii) cells of different cell lineages; or (iv) cells from different cell cultures, wherein the cultures have been subjected to different culture conditions, wherein said one or said plurality of reference biomolecules are a metabolically isotope labeled form of said one or said plurality of first biomolecules, and wherein said biomolecules are proteins or peptides.

As is apparent from this preferred embodiment, pre-filled sample preparation containers are of particular interest. Given that item (a) of the above disclosed preferred embodiment provides for one, two, three, four, five, six, seven or all of the specified options, the claim inherently specifies a limited number of sub-combinations of agents or conditions to be established in said sample preparation container. Particularly preferred sub-combinations are the following. Each of the sub-combinations given below relate to bio-organic compounds (herein also referred to as "analytes") which are or comprise one or more proteins, peptides and/or polypeptides.

Preferred enzymes are proteases. Preferred proteases are one out of or a combination of Lys-C, Trypsin, AspN, GluC, and Chymotrypsin. As disclosed above, trypsin and Lys-C, either alone or a combination thereof, are particularly preferred. As is apparent from this preferred embodiment, pre-filled sample preparation containers are of particular interest. Given that item (a) of the above disclosed preferred embodiment provides for one, two, three, four, five, six, seven or all of the specified options, the claim inherently specifies a limited number of sub-combinations of agents or conditions to be established in said sample preparation container. Particularly preferred sub-combinations are the following. Each of the sub-combinations given below relate to bio-organic compounds (herein also referred to as "analytes") which are or comprise one or more proteins, peptides and/or polypeptides.

(1) A sample preparation container, wherein said container comprises, preferably as the only reagents, an alkylating agent, a reducing agent, a detergent, and the pH-value in said container is between 8 and 9. Particularly preferred is a sample preparation container comprising, preferably as the only reagents, CAA, TCEP, SDC, and Tris buffer at pH 8.5.

(2) Above embodiment (1), wherein said container further comprises a standard for mass-spectrometric analysis, preferably a SILAC standard or a SUPER-SILAC standard.

(3) The embodiment in accordance with (1) or (2), furthermore comprising a glycosidase, a preferred glycosidase being PNGase F.

In accordance with the above disclosed preferred embodiment, said particularly preferred embodiments (1) to (3) at the same time define also preferred implementation of the method in accordance with the present invention. As disclosed herein, it is preferred that a protease or a mixture of proteases is added immediately prior to performing proteolysis, i.e., after lysis, reduction and alkylation has been effected.

Accordingly, it is understood that the present invention provides, in a further aspect, a closed sample preparation container, the container comprising a reaction chamber and a chromatography medium; wherein said reaction chamber comprises, preferably as the only reagents, an alkylating agent, a reducing agent, a detergent, and the pH-value in said container is between 8 and 9; wherein (a) said chromatography medium is located at a wall of said reaction chamber, and said wall is closed or sealed and configured to be opened; or (b) said sample preparation container further comprises a receiving chamber, said receiving chamber being adjacent to said chromatography medium such that said chromatography medium separates said reaction chamber from said receiving chamber, and the outer face of said receiving chamber is closed and configured to be opened. Particularly preferred alkylating agents, reducing agents and detergents as well as pH-values are those in accordance with the particularly preferred embodiments (1) to (3) as defined herein above.

A preferred nucleic acid in accordance with item (b) is mRNA. A preferred reaction to be performed with said reagents for nucleic acid amplification is the creation of a RNA Poly(A) library for RNA-seq (also referred to as "RNA deep sequencing" in the art) analysis from a plurality of mRNAs comprised in said cellular material, viruses and/or sub-components of said cellular material and/or viruses. Preferred reagents for nucleic acid amplification are RT-PCR suitable salts, deoxy-nucleotides (dNTPs), primers (commonly poly-dT primers), and a reverse transcriptase.

In a further preferred embodiment of both the first and the third aspect of the present invention, said container further comprising (a) at least one of the following chemicals: milling beads, detergents, preferably detergents which are known not to interfere with chromatography, chaotropic agents such as urea, thiourea or guanidinium hydrochloride (GdmCl), alkylating agents such as iodoacetamide and chloroacetamide, reducing agents such as dithiothreitol (DTT) or tris(2-carboxyethyl)phosphine (TCEP), organic solvents such as acetonitrile or methanol, standards for mass-spectrometric analysis such as a SUPER-SILAC mix as described further above; and/or (b) at least one of the following enzymes: protease, nuclease, decarboxylase.

A preferred chaotropic agent is GdmCl.

In a further preferred embodiment of both the first and third aspect of the present invention, (a) said cellular material is one of: intact cells, non-clarified cell lysate, tissue, pathogens; and/or (b) said sub-components are sub-cellular structures, in particular organelles. Exemplary organelles are mentioned further above.

It is understood that non-clarified cell lysate comprises debris, such debris typically being formed in the course of disruption said cellular material, viruses and/or sub-components of said cellular material and/or viruses.

In a further preferred embodiment of the method of the invention, to the extent said bio-organic compounds are proteins, peptides or polypeptides, step (b) of said method further comprises reduction and alkylation.

In a further preferred embodiment of the method of the invention, step (b) of said method further comprising proteolytic digestion. It is preferred that proteolytic digestion is affected after reduction and alkylation. It is furthermore preferred that the one or more proteases required for proteolytic digestion are added to the container or the reaction mixture immediately prior to performing said proteolytic digestion, i.e., after reduction and alkylation has been affected. To the extent the present invention relates to pre-filled sample preparation containers, i.e., sample preparation containers which already comprise one or more reagents, it is accordingly preferred that a protease is not among the agents comprised in the pre-filled sample preparation container.

In a further preferred embodiment, said obtaining said purified and/or enriched bio-organic compounds in said receiving chamber is effected by (i) allowing the products of step (b) to enter and be retained in said chromatographic medium, and (ii) eluting said bio-organic compounds.

Once said cellular material, viruses and/or sub-components of said cellular material and/or viruses has been disrupted, and preferably also subjected to the further processing steps detailed herein above, said preferred further processing steps including reduction, alkylation and proteolytic digestion, the mixture present in said reaction chamber is allowed to pass through said chromatographic medium. Typically, high molecular weight material, at this stage of the processing to be viewed as contaminants, will be retained within the reaction chamber, more specifically at the surface of the chromatographic medium facing said reaction chamber. On the other hand, low molecular weight compounds such as salt and furthermore reducing agents and alkylating agents, to the extent they may be present, will pass through to chromatographic medium. The chromatographic medium will generally retain the bio-organic compounds, preferably said peptides, polypeptides and peptides. To the extent proteolytic digestion has been effected, said bio-organic compounds, at this stage of the processing, will generally be present in the form of peptides. For the purpose of elution in accordance with step (ii) of the preferred embodiment disclosed above, art-established eluents may be used which are described, for example, in Rappsilber et al. (loc. cit.). To provide preferred examples, we note that acetonitrile or methanol may be used in case the chromatographic medium is reversed phase material such as C18 or C8 material. Ammonia, ammonium acetate or ammonium formeat may be used in case SCX has been used as chromatographic material. Formic acid, acetic acid and/or sodium chloride may be used in case SAX has been used as chromatographic medium. Further eluents may be chosen by the skilled person without further ado and depending on the chromatographic medium.

In a further preferred embodiment of the method in accordance with the third aspect of the invention, said container is a container in accordance with embodiment (b) of the first aspect of the present invention.

In a fourth aspect, the present invention provides a kit comprising or consisting of (a) a sample preparation container according to the first aspect of the invention; and (b)(i) a protease, an alkylating agent, a standard for mass-spectrometric analysis and/or means for establishing a pH-value in said container of between 8 and 9, preferably 8.5; and/or (ii) a nuclease, preferably an endonuclease; and/or reagents for nucleic acid amplification, preferably by PCR.

Related thereto, the present invention provides a kit comprising or consisting of (a) a sample preparation container according to the first aspect of the invention; and (b) (i) a protease, preferably trypsin and/or Lys-C; an alkylating agent, preferably chloroacetamide; a reducing agent, preferably TCEP; a standard for mass-spectrometric analysis; a chaotropic agent, preferably GdmCl, or a detergent, preferably SDC; and/or means for establishing a pH-value in said container of between 7 and 9, preferably 8 and 9, more preferably 8.5; and/or (ii) a nuclease, preferably an endonuclease; and/or reagents for nucleic acid amplification, preferably by PCR.

As explained further above, a container in accordance with the present invention may be pre-filled with one or more agents. As an alternative, an empty or only partially pre-filled container may be provided as component (a) of the kit according to the invention, while the agent suitable for purifying and/or enriching given bio-organic compounds may be provided as separate further component(s) of the kit according to the invention.

In a preferred embodiment of the kit, it further comprises (a) at least one of the following chemicals: bead-milling material, detergents, chaotropic agents, alkylating agents such as iodoacetamide, reducing agents, organic solvents, standards for mass-spectrometric analysis; (b) at least one of the following enzymes: protease, nuclease, kinase, glycosidase; and/or (c) a manual with instructions for performing the method according to the third aspect of the present invention.

In a preferred embodiment of the kit, it further comprises (a) at least one of the following chemicals: bead-milling material, detergents, chaotropic agents, alkylating agents such as iodoacetamide, reducing agents, organic solvents, antioxidants, UV-absorbants, standards for mass-spectrometric analysis; (b) at least one of the following enzymes: protease, nuclease, kinase, glycosidase; and/or (c) a manual with instructions for performing the method according to the third aspect of the present invention.

In a fifth aspect, the present invention provides a system comprising (a) a sample preparation container according to the invention in accordance with item (a) of the main embodiment; and (b) a receiving chamber according to the second aspect of the invention.

BRIEF DESCRIPTION OF THE DRAWINGS

The figures show.

(100) Sample preparation container.

(101) A self-sealing rubber lid or rubber plug can be penetrated by a needle or needles to introduce samples, chemicals or shield gas. The rubber plug reseals after removal of the needle.

(102) A reaction chamber is constructed for certain reactions such as cell lysis by sonication, protein alkylation, e.g. by iodoacetamide, and proteolysis.

(103) A surface of the chromatography medium acts as filtration surface. Other surfaces could be applied on top or instead of the filtration surface, for example a non-binding filtration matrix such as microporous Millipore filter.

(104) A chromatography medium is used to bind, purify and enrich the cellular material of interest. The matrix can be designed to perform multidimensional chromatography which may be effected by using multiple stacks of chromatography media.

(105) A seal is used to completely seal the reaction chamber before sample lysis. The seal can be opened for washing, purification and elution steps.

(100) Sample preparation container.

(101) A self-sealing rubber lid or rubber plug can be penetrated by a needle or needles to introduce samples, chemicals or shield gas. The rubber plug reseals after removal of the needle.

(102) A reaction chamber is constructed for certain reactions such as cell lysis by sonication, protein alkylation, e.g. by iodoacetamide, and proteolysis.

(103) A surface of the chromatography medium acts as filtration surface. Other surfaces could be applied on top or instead of the filtration surface, for example a non-binding filtration matrix such as microporous Millipore filter.

(104) A chromatography medium is used to bind, purify and enrich the cellular material of interest. The matrix can be designed to perform multidimensional chromatography which may be effected by using multiple stacks of chromatography media.

(107) A wall which is closed and sealed, the wall being configured to be opened for obtaining purified and/or enriched bio-organic compounds.

(108) Screw thread, e.g. a female screw thread, configured to be coupled with a corresponding screw thread, e.g. a male screw thread.

(200) Receiving chamber configured to receive said purified and/or enriched bio-organic compounds. The upper side of the receiving chamber may be open or sealed.

(208) Screw thread, e.g. a male screw thread, configured to be coupled with a corresponding screw thread, e.g. a female screw thread.

(208a) Sharp-edged extension at the end of the screw thread of the receiving chamber which penetrates the wall of the sample preparation container when the screw thread of the receiving chamber is tightly screwed in the corresponding screw thread of the preparation container.

(a) Frequency of protein identification of four biological replicates. Proteins identified in all four runs are designated as core proteome. (b) MS-signals (Label-free quantification (LFQ) intensities from the MaxQuant output) of five representative proteins spanning the entire dynamic range) in four biological replicates (c) Comparison of LFQ intensities determined in single-shot analysis to LFQ intensities determined in 6-fraction analysis.

(a) Comparison of identified proteins using 6-fraction iST-SCX analysis to the deepest experimental *S. cerevisiae* proteome (Peng et al., *Nature methods* 9 (6), 524 (2012)). (b) Correlation of estimated copy numbers using 6-fraction iST-SCX analysis to copy numbers reported using 21 synthetic peptide standards (Picotti et al., *Cell* 138 (4), 795 (2009)). (c) Distribution of estimated copy numbers. Vertical red line indicates 100 copies per cell. Blue bins represent proteins that are identified uniquely in the 6-fraction iST-SCX analysis. (d) Comparison of identified proteins using 6-fraction iST-SCX analysis to proteins reported in a recent study presenting the deepest proteome of *S. pombe* (Gunaratne et al., *Molecular & cellular proteomics* (12(6):1741-51 (2013)). (e) Correlation of estimated copy numbers using 6-fraction iST-SCX analysis to copy numbers reported in another recent in-depth analysis of *S. pombe* (Marguerat et al., *Cell* 151 (3), 671 (2012)).

The following examples illustrate the invention but should not be construed as being limiting.

EXAMPLE 1

Purification of Peptides for Proteomics Analysis Using Mass Spectrometry

The system has been tested in the field of proteomics using completely sealed tubes or tubes only sealed at one side (usually the bottom, the bottom being the location of the receiving chamber or where the receiving chamber may be attached, respectively). Cells were lysed within the described tube as well as outside the tube without any notable disadvantages for in-tube lysis. Contained proteins were proteolytically digested and crude contaminants were filtered on the surface of the reversed-phase purification matrix C18, which was embedded in Teflon material. The peptides were enriched and desalted on the C18 material. Clean peptides were eluted from the C18 material and subsequently analyzed by LC-MS/MS.

The results demonstrate high stability and the ability to scale up or down in terms of sample quantities. The efficiency was highly increased, such that no loss was observed. The efficiency of the approach enables the processing of few single cells, which was not possible by established state of the art techniques as shown by processing of as few as 500 HeLa S3 cells. The processing speed is highly increased compared to current methods with a complete sample preparation within 1 h time compared to at least approximately 4 h time, or more commonly 12 h, with other state of the art methods. Expert knowledge is not required because every step is simplified and the source for failure is reduced to a minimum. Very few unwanted modifications of analytes (oxidation, modification by UV light etc.) were observed. Reproducibly high identification rates were observed by LC-MS analysis (MS/MS ID rate of 60%). The amount of contaminations was significantly reduced, also when working with low quantity samples. Polymers or plastics may occur as source of contamination, owing to one or more transfer steps as required for previously known procedures. Sample preparation may involve working with harmful and poisonous chemicals such as DTT and iodoacetamide, which can be provided in a pre-filled and sealed container of the invention, thereby reducing the risk of harm. The separate materials, which could be used to produce the reaction vessels are well known and described and could be combined in a very cheap manner. An automated version of the system is feasible and can easily be implemented.

EXAMPLE 2

Copy Numbers in *S. cerevisiae* and *S. pombe*

Figure 4:
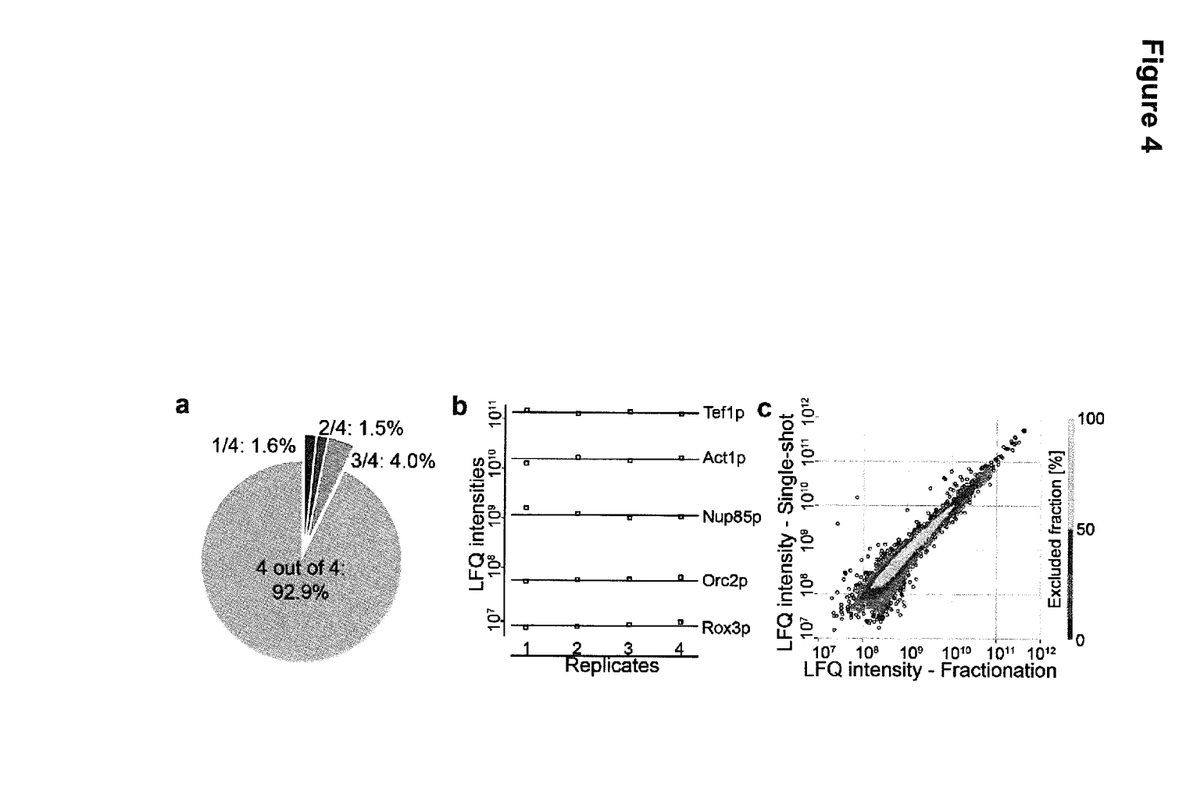
FIG. 4: Quantitative reproducibility of in-depth *S. cerevisiae* proteome and copy number estimation.

Protein copy numbers are of great interest to the biological and systems biological communities and we reasoned that a streamlined, minimalistic sample processing method could provide particularly unbiased values. To evaluate the minimalistic sample processing method on the well characterized yeast model system we grew *S. cerevisiae* in four biological replicates and processed them in parallel in the 96-well format (100 uL culture at $OD_{600}$=0.8). Four single-run analyses together identified 4,270 distinguishable protein groups and remarkably, 97% of them were detected in at least three of the four replicates with high quantitative reproducibility (Total median sequence coverage: 34.4%, total number of unique peptide IDs: 46,125; FIG. 4*a, b*). In our recent yeast proteome analysis in single-run mode, which used the same downstream LC-MS/MS set-up (Nagaraj et al., *Molecular & cellular proteomics: MCP* 11 (3), M111 013722 (2012)), mean identification in each individual run were 4,084 protein groups (33,122±405 sequence-unique peptide identifications, median seq. coverage 23.4%), whereas the minimalistic processing method produced an even higher numbers (4,144 protein groups, 37,880±1771 sequence-unique peptides, median sequence coverage 27.2%).

SCX-fractionation of a yeast sample directly from the reaction device into six autosampler vials, followed by essentially the same LC-MS/MS analysis as before, quantified 4,577 protein groups, the largest expressed yeast proteome reported to date. Importantly, we did not identify any of the 656 dubious open reading frames, which are thought not to represent expressed messages or proteins. Excellent correlation of label-free intensity values with those of a single-run analysis ($R^2=0.91$), shows that in-StageTip fractionation did not introduce any biases, even in the very low intensity region (FIG. 4c).

Figure 5:
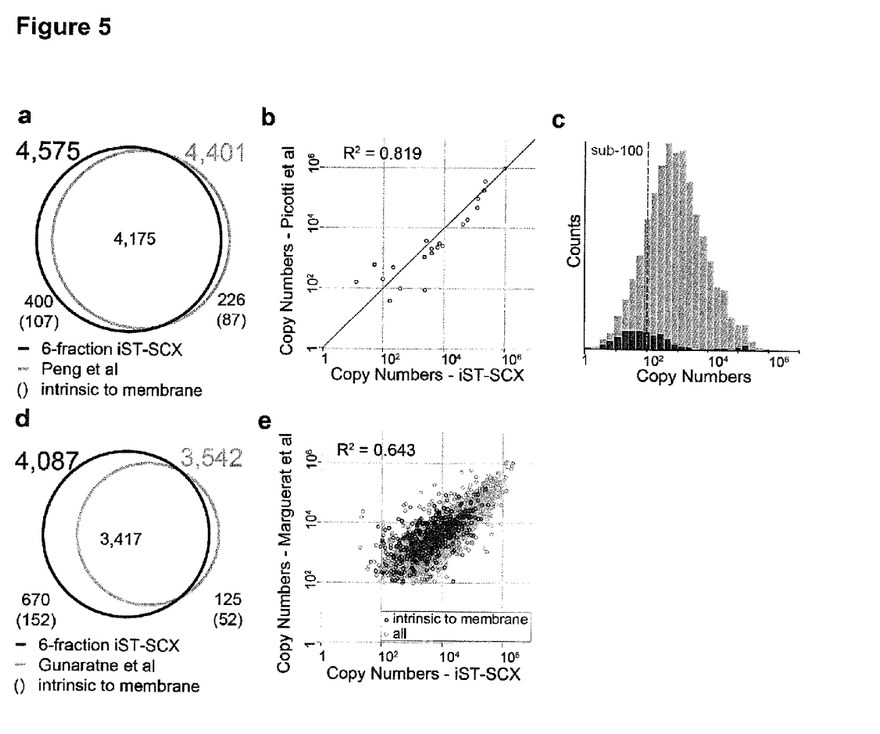
FIG. 5: In-depth coverage of yeast proteomes and estimation of yeast copy numbers. (a), (b) and (c) based on *S. cerevisiae* dataset. (d) and (e) based on *S. pombe* dataset.

The deepest previous proteome of exponentially growing *S. cerevisiae* used five different proteolytic enzymes as well as extensive, column-based SCX fractionation of peptides (Peng et al., *Nature methods* 9 (6), 524 (2012)). Our single six-fraction dataset largely encompassed the previous study (94.9%) and added 400 proteins, among which intrinsic membrane proteins were significantly enriched ($p=9.4 \times 10^{-6}$) (FIG. 5a). We next used the label-free MS-signal for each protein as a fraction of the total MS-signal of the proteome (Wisniewski et al., *Molecular systems biology* 8, 611 (2012)) to estimate copy numbers for 4,570 yeast proteins. Copy numbers have previously been established for 21 yeast proteins using synthetic peptide standards6 and our values agree well within the expected uncertainties ($R^2=0.82$) (FIG. 5b). The most abundant yeast protein, at $1.6 \times 10^6$ copies per cell, was the glycolytic enzyme Tdh3p, which is encoded in three genomic loci. The median yeast protein had approximately 800 copies per cell and a copy number range of a factor of 2000 contained more than 90% of the proteins. The six ORC complex members have a median copy number of 332±150, an interesting relation to the estimated 500 origins of replication in *S. cerevisiae* (Nieduszynski et al., *Nucleic acids research* 35 (Database issue), D40 (2007)).

We were intrigued that more than 763 yeast proteins had less than 100 copies per cell (FIG. 5c), a much larger proportion than in a classical study of yeast copy numbers (Ghaemmaghami et al., *Nature* 425 (6959), 737 (2003)). This population was significantly enriched for the GO terms cell cycle process and DNA repair ($p<9 \times 10^{-10}$ and $<1.8 \times 10^{-4}$, respectively).

For very low abundance proteins, a weak MS signal may introduce uncertainties, nevertheless we measured largely consistent copy numbers for members of the anaphase promoting complex (APC), indicating about 30 APCs per cell. Proteins only present in certain cellular states were often found with very low apparent copy numbers such as the cyclin CLB2 (G2/M phase), at 100 copies or the kinase inhibitor FAR1 (G1 phase) at about 50 copies. This illustrates that our dataset already includes contributions from several different proteomic states.

*S. pombe* diverged from *S. cerevisiae* more than 400 million years ago and provides an interesting comparative model. The deepest proteomic study of that organism very recently employed several growth conditions and very extensive, orthogonal fractionation to identify 3,542 proteins (Gunaratne et al., *Molecular & cellular proteomics: MCP* (2013)). Using the six-fraction approach on exponentially growing cells only, we obtained 4,087 proteins searching against the same database. This represents 80% of *S. pombe* ORFs and covers 96.5% of the previous proteome as well as 670 additional, generally low-abundance ones (FIG. 5d). In reference to another deep *S. pombe* proteome (Marguerat et al., *Cell* 151 (3), 671 (2012)), our *S. pombe* copy numbers agreed very well with those reported for 34 proteins for which isotope labeled standards had been synthesized ($R^2=0.89$) and there was no apparent bias against any protein class, including intrinsic membrane proteins (FIG. 5e). The most abundant proteins had around $10^6$ copies per cell, similar to *S. cerevisiae*, but the proportion below 100 copies was much reduced (17% vs. 3%). Median copy number was 5,137, about six-fold higher than in *S. cerevisiae*. The lowest expressed 5% of the proteome was significantly enriched for replication fork processing and DNA repair related proteins ($p<1.1\times10^{-6}$ and $<1.2\times10^{-6}$, respectively). This fraction of the proteome contains many so far uncharacterized *S. pombe* ORFs (59 of 207 proteins; $p<3.9 \times 10^{-5}$).

The invention claimed is:

1. A method of preparing purified and/or enriched bio-organic compounds from cellular material, viruses and/or sub-components of said cellular material and/or viruses, said method comprising
   (a) introducing said cellular material, viruses and/or sub-components of said cellular material and/or viruses, comprising proteins, into a reaction chamber of a container, said container further comprising a chromatographic medium and a receiving chamber, said receiving chamber being adjacent to said chromatography medium, said chromatographic medium separating said reaction chamber from said receiving chamber, wherein an outer face of said receiving chamber is closed and configured to be opened for obtaining said purified and/or enriched bio-organic compounds;
   (b) disrupting said cellular material, viruses and/or sub-components of said cellular material and/or viruses inside said reaction chamber;
   (c) performing proteolytic digestion;
   (d) eluting said bio-organic compounds,
   thereby obtaining said purified and/or enriched bio-organic compounds in said receiving chamber;
wherein the bio-organic compounds comprise at least one of peptides, polypeptides, nucleic acids, lipids, or metabolites;
wherein said disrupting is effected by
   (i) sonication;
   (ii) boiling in the presence of a chaotropic agent and/or a denaturing agent; and/or
   (iii) bead milling;
   and
   wherein said method is exclusively performed in said container.

2. The method of claim 1, wherein said disrupting is effected by bead milling.

3. The method of claim 1, wherein step (c) of said method further comprises reduction and alkylation.

* * * * *